US009213006B2

(12) United States Patent
Wood

(10) Patent No.: US 9,213,006 B2
(45) Date of Patent: Dec. 15, 2015

(54) MODULATED X-RAY HARMONIC DETECTION

(71) Applicant: Lockheed Martin Corporation, Bethesda, MD (US)

(72) Inventor: James Richard Wood, Grapevine, TX (US)

(73) Assignee: Lockheed Martin Corporation, Bethesda, MD (US)

(*) Notice: Subject to any disclaimer, the term of this patent is extended or adjusted under 35 U.S.C. 154(b) by 3 days.

(21) Appl. No.: 14/362,276

(22) PCT Filed: Nov. 30, 2012

(86) PCT No.: PCT/US2012/067217
§ 371 (c)(1),
(2) Date: Jun. 2, 2014

(87) PCT Pub. No.: WO2013/082374
PCT Pub. Date: Jun. 6, 2013

(65) Prior Publication Data

US 2014/0355741 A1 Dec. 4, 2014

Related U.S. Application Data

(60) Provisional application No. 61/566,584, filed on Dec. 2, 2011.

(51) Int. Cl.
*G01N 23/20* (2006.01)
*G01N 23/203* (2006.01)
(Continued)

(52) U.S. Cl.
CPC ........ *G01N 23/203* (2013.01); *G01N 23/20008* (2013.01); *G01V 5/0025* (2013.01); *G21K 1/00* (2013.01); *G01N 2223/053* (2013.01)

(58) Field of Classification Search
CPC ............ A61B 6/483; G01N 23/20058; G01N 23/203; G01N 2223/053; G01N 2223/056; G01N 2223/0566; G01N 2223/304; G01N 2223/345; G01N 2223/41; G01N 2223/425; G01N 2223/426; G01N 2223/625; G01N 2223/626; G01N 2223/639; G01V 5/0008; G01V 5/0016; G01V 5/0025
See application file for complete search history.

(56) References Cited

U.S. PATENT DOCUMENTS 4,035,616 A 7/1977 Piringer
4,385,549 A 5/1983 Bauer et al.
(Continued)

FOREIGN PATENT DOCUMENTS

JP 5142396 A 6/1993
WO 2013082374 A1 6/2013

OTHER PUBLICATIONS

Carter et al., "A Microchannel Plate Intensified, Subnanosecond, X-ray Imaging Camera," Physica Scripta, vol. 41, pp. 390-395, 1990.
(Continued)

*Primary Examiner* — Thomas R Artman
(74) *Attorney, Agent, or Firm* — Withrow & Terranova, PLLC

(57) ABSTRACT

The presently disclosed technique provides a method and apparatus for use in modulated X-ray harmonic detection and identification. More specifically, it specifies a X-ray backscatter imaging system using radio frequency modulation of the incident X-ray beam at two frequencies and detection patterns in the backscattered signal corresponding to harmonics of the modulation frequencies.

20 Claims, 3 Drawing Sheets

100 110 140 120 130

242 239 209 206 203 245 244 238 215 218 237 212

RF MODULATOR
SOURCE
SYNC
RF MODULATOR
SENSOR
IMAGE

(51) Int. Cl.
*G01V 5/00* (2006.01)
*G21K 1/00* (2006.01)

(56) References Cited

U.S. PATENT DOCUMENTS 4,881,549 A * 11/1989 Rhyne ........................ 600/443
4,935,616 A 6/1990 Scott
5,044,006 A 8/1991 Cyrulnik
5,206,592 A 4/1993 Buess et al.
5,592,083 A 1/1997 Magnuson et al.
5,608,403 A 3/1997 Miller
5,635,721 A 6/1997 Bardi et al.
5,642,393 A 6/1997 Krug et al.
5,696,577 A 12/1997 Stettner et al.
5,751,830 A 5/1998 Hutchinson
5,754,290 A 5/1998 Rajic et al.
5,760,403 A 6/1998 Elabd
6,088,423 A 7/2000 Krug et al.
6,194,898 B1 2/2001 Magnuson et al.
6,531,225 B1 3/2003 Homme et al.
6,544,458 B1 * 4/2003 Hansma ...................... 264/234
6,762,420 B2 7/2004 Homme et al.
6,952,163 B2 10/2005 Huey et al.
7,023,956 B2 4/2006 Heaton et al.
7,130,371 B2 10/2006 Elyan et al.
7,135,672 B2 11/2006 Land
7,142,109 B1 11/2006 Frank
7,231,017 B2 6/2007 Gertsenshteyn et al.
7,317,390 B2 1/2008 Huey et al.
7,327,137 B1 2/2008 Crowley et al.
7,344,304 B2 3/2008 Hardesty
7,368,292 B2 5/2008 Hummel et al.
7,385,549 B2 6/2008 Lovberg et al.
7,433,054 B1 10/2008 Tischhauser et al.
7,453,552 B1 11/2008 Miesak
7,646,851 B2 1/2010 Liu et al.
8,111,808 B1 2/2012 Wood
8,411,820 B1 4/2013 Browder et al.
8,411,821 B1 4/2013 Wood et al.
8,433,037 B1 4/2013 Wood
8,983,034 B2 * 3/2015 Wood ............................ 378/88
2003/0144800 A1 7/2003 Davis et al.
2004/0165187 A1 8/2004 Koo et al.
2004/0257224 A1 12/2004 Sajkowsky
2005/0079386 A1 4/2005 Brown, Jr. et al.
2005/0099292 A1 5/2005 Sajkowsky
2005/0104603 A1 5/2005 Peschmann et al.
2006/0022140 A1 2/2006 Connelly et al.
2006/0145812 A1 7/2006 Sajkowsky
2007/0008135 A1 1/2007 Sajkowsky
2007/0025512 A1 2/2007 Gertsenshteyn et al.
2007/0211922 A1 9/2007 Crowley et al.
2008/0111545 A1 5/2008 Crowley
2008/0120430 A1 5/2008 Redmond
2012/0141009 A1 * 6/2012 Wood ......................... 382/132
2014/0133631 A1 * 5/2014 Wood ........................... 378/88
2014/0355741 A1 * 12/2014 Wood ........................... 378/86
2015/0168137 A1 * 6/2015 Pauly ........................... 378/70

OTHER PUBLICATIONS

Notice of Allowance for U.S. Appl. No. 12/541,539 mailed Sep. 28, 2011, 8 pages.

Non-final Office Action for U.S. Appl. No. 12/541,539 mailed Feb. 10, 2011, 8 pages.

Kozyrev, A.B. et al., "Nonlinear Behavior of Thin Film SrTiO3 Capacitors at Microwave Frequencies," Journal of Applied Physics, vol. 84, Issue 6, Sep. 1998, American Institute of Physics, pp. 3326-3332.

Runkle, Robert C. et al., "Photon and neutron interrogation techniques for chemical explosives detection in air cargo: A critical review," Nuclear Instruments and Methods in Physics Research, Section A: Accelerators, Spectrometers, Detectors and Associated Equipment, vol. 603, Issue 3, May 21, 2009, Elsevier B.V., pp. 510-528.

Yu, Y.H. et al., "Measurement of Thin Film Piezoelectric Constants Using X-ray Diffraction Technique," Physica Scripta, vol. 2007, T129, Dec. 2007, IOP Publishing, pp. 353-357.

International Search Report and Written Opinion for PCT/US2012/067217, mailed Mar. 28, 2013, 14 pages.

International Preliminary Report on Patentability and Written Opinion for PCT/US2012/067217, mailed Jun. 12, 2014, 8 pages.

Non-final Rejection for for U.S. Appl. No. 12/604,548, mailed Feb. 22, 2011, 11 pages.

Final Office Action for U.S. Appl. No. 12/604,548, mailed Jun. 3, 2011, 11 pages.

Non-final Rejection for for U.S. Appl. No. 12/604,548, mailed Oct. 25, 2012, 11 pages.

Notice of Allowance for U.S. Appl. No. 12/604,548, mailed Feb. 8, 2013, 5 pages.

Non-Final Office Action for U.S. Appl. No. 13/368,257, mailed Mar. 27, 2014, 4 pages.

Notice of Allowance for U.S. Appl. No. 13/368,257, mailed Jul. 18, 2014, 9 pages.

Notice of Allowance and Examiner-Initiated Interview Summary for U.S. Appl. No. 13/368,257, mailed Oct. 31, 2014, 9 pages.

Non-Final Office Action for U.S. Appl. No. 14/158,152, mailed Aug. 11, 2015, 7 pages.

* cited by examiner

MODULATED X-RAY HARMONIC DETECTION

This application is a 35 U.S.C. §371 national phase filing of International Application No. PCT/US12/67217, filed on Nov. 30, 2012, which claims priority under 35 U.S.C. §119(e) from U.S. Provisional Application No. 61/566,584 filed on Dec. 2, 2011, the disclosures of which are hereby incorporated herein by reference in their entireties.

BACKGROUND

This section of this document introduces various pieces of the art that may be related to or provide context for some aspects of the technique described herein and/or claimed below. It provides background information to facilitate a better understanding of that which is disclosed herein. This is a discussion of "related" art. That such art is related in no way implies that it is also "prior" art. The related art may or may not be prior art. The discussion in this section is to be read in this light, and not as admissions of prior art.

Detection of the stress in and resulting strained states of thin film materials and small volume samples of material are difficult to resolve by looking at diffraction patterns/shadowgraphs in 2D angle space. The detection of such diffraction pattern shifts between strained conditions, uses X-ray, electron, and neutron diffraction techniques that require careful sample preparation. Furthermore, preferred orientations may not always be available for investigation of novel materials and structures in situ.

The presently claimed subject matter is directed to resolving, or at least reducing, one or all of the problems mentioned above.

SUMMARY

The presently disclosed technique provides a method and apparatus for use in modulated X-ray harmonic detection and identification.

In a first aspect, a method comprises: modulating an X-ray signal with as first radio frequency and with a second radio frequency; transmitting the modulated X-ray signal into a field of view containing a sample; receiving backscatter of the transmitted X-ray signal reflected from the sample; and processing the received backscatter to identify the sample from the pattern of the detected harmonics of the first and second radio frequency signals.

In a second aspect, an X-ray RADAR apparatus comprises: means for modulating an X-ray signal with a first radio frequency and with a second radio frequency; means for transmitting the modulated X-ray signal into a field of view containing a sample; means for receiving backscatter of the transmitted X-ray signal reflected from the sample; and means for processing the received backscatter to identify the sample from the pattern of the detected harmonics of the first and second radio frequency signals.

In a third aspect, a computer-implemented method, comprising: receiving data representative of backscatter of a radio frequency modulated X-ray signal reflected from a sample, the X-ray signal being radio frequency modulated with a first frequency and with a second frequency; and processing the received backscatter to identify the sample from the pattern of the detected harmonics of the first and second radio frequency signals.

In a fourth aspect, a program storage medium encoded with instructions that, when executed by a processor, perform a software implemented method, the software implemented method comprising: receiving data representative of backscatter of a radio frequency modulated X-ray signal reflected from a sample, the X-ray signal being radio frequency modulated with a first frequency and with a second frequency; and processing the received backscatter to identify the sample from the pattern of the detected harmonics of the first and second radio frequency signals.

In a fifth aspect, a computing apparatus, comprises: a processor; a bus system; a storage communicating with the processor over the bus system; and an application residing on the storage that, when invoked, by the processor, performs a software implemented method, comprising: receiving data representative of backscatter of a radio frequency modulated X-ray signal reflected from a sample, the X-ray signal being radio frequency modulated with a first frequency and with a second frequency; and processing the received backscatter to identify the sample from the pattern of the detected harmonics of the first and second radio frequency signals.

In a sixth aspect, an X-ray RADAR apparatus, comprises: a transmitter capable of: modulating an X-ray signal with a first radio frequency and with a second radio frequency; and transmitting the modulated. X-ray signal into a field of view; a receiver capable of receiving backscatter of the transmitted X-ray signal reflected from a sample within the field of view; and a processing unit capable of processing the received backscatter to identify the sample from the pattern of the detected harmonics of the first and second radio frequency signals.

The above presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the invention are described below. In the interest of clarity, not all features of an actual implementation are described in this specification. It will of course be appreciated that in the development of any such actual embodiment, numerous implementation-Specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Figure 1:
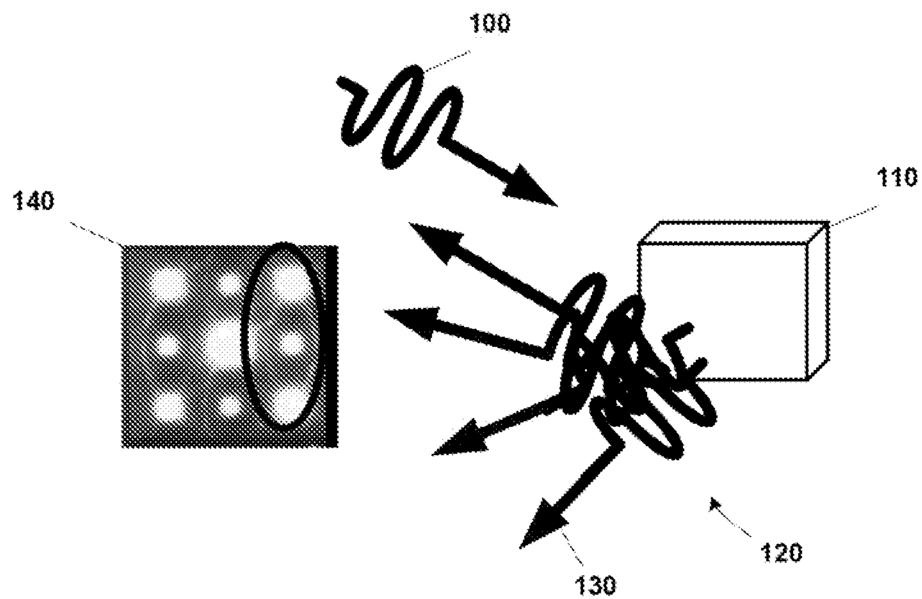
FIG. 1 conceptually illustrates one particular embodiment with which the presently disclosed technique may be practiced.

Turning now to FIG. 1, a modulated X-ray signal 100 is directed toward a sample 110. The signal 100 may be modulated as discussed further below and as disclosed in the applications incorporated by reference below. The sample 110 reflects and, in the illustrated embodiment, diffracts the signal 100 into a diffraction pattern 120. The diffraction pattern elements 130 (only one indicated) contain not only the carrier the signal 100), but also various harmonics thereof. The scattering patterns therefore contain additional information in the frequency domain to identify which patterns contain information scattered from a thin film or small volume region. This additional information identifies the strained state and indicates stress in the material. Modulated x-ray energy is scattered from a sample of material, the scattered x-ray energy containing nonlinear frequency domain response from the photocurrent stresses generated by the x-ray flux.

More particularly, the scattered energy contains the fundamental modulation of the x-ray energy, plus additional second and third harmonics and their mixing products with the fundamental or "carrier" x-ray modulation frequency. The amounts of energy in the scattered harmonic products provide additional information on the state of the sample under x-ray examination.

Note, however, the presently disclosed technique is not limited to diffraction. The illustrated embodiment shows how lattice changes would show up in the "blur spot" intensity changes, without having to show a "blur" image. The nonlinear material response in the detected x-ray intensity would be a combination/superposition of diffraction shadows, transmissivity changes and reflectivity changes in and along surfaces that change in a nonlinear way with the x-ray signal.

FIG. 1 includes a depiction of a rendered image 140. It is not necessary to render or even use images, but one can do harmonic detection on selected "pixels" in an image, as long as the pixels are co-sighted/aligned with the harmonic x-ray signal detector. Most applications would benefit by having knowledge of an x-ray image and location of given harmonic content in certain parts of the x-ray image. (The harmonics can be detected separately from the imager system.) The knowledge of relative location and harmonic content (nonlinear material locations) would be useful in some embodiments.

Figure 2:
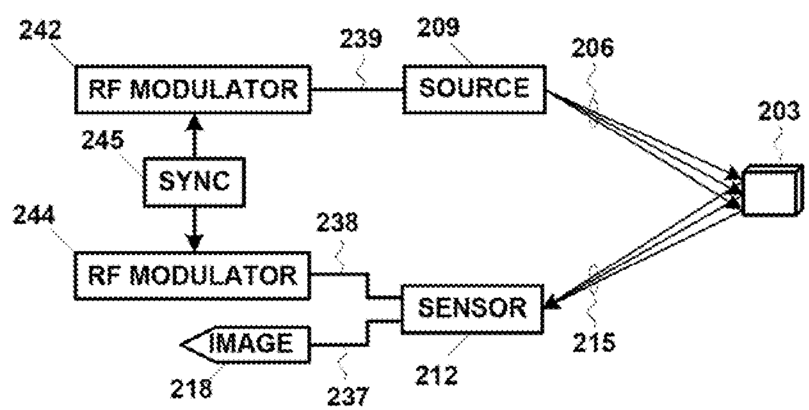
FIG. 2 conceptually depicts one particular embodiment of an X-ray microscopy imaging system.

FIG. 2 illustrates one particular embodiment of an apparatus 200 by which the method of the presently disclosed technique may be performed. This system images the received backscatter from the sample although, as set forth above, imaging is not necessary in all embodiments. More particularly, FIG. 2 conceptually illustrates one particular embodiment of an X-ray microscopy imaging system 200. The system 200 is shown subjecting a target volume, or specimen, 203 to a plurality of X-rays 206 (only one indicated) generated and radio-frequency modulated as discussed further below. The system 200 comprises, in general, an X-ray source 209 and a sensor 212.

The X-ray source 209 is capable of emitting the plurality radio-frequency modulated X-rays 206 toward the target volume 203 when in operation. The sensor 212 is capable of imaging a plurality of X-rays 215 (only one indicated) reflected from the target volume 203 and radio-frequency modulating the image when in operation. Radio frequency modulating the image impresses the image with a radio-frequency modulation. Upon imaging the X-rays 215, the sensor 212 then outputs the radio-frequency modulated image 218.

In general, the X-ray source 209 of the illustrated embodiment includes a filament, a radio-frequency modulated tube, and a high power microwave source, none of which are shown. The filament generates an electron beam output to the radio frequency modulated tube. The radio frequency modulated tube comprises a pair of cavity resonator structures and a high power (e.g., 2 joules/pulse) microwave source that give rise to the magnetic or electric fields that deflect the electron beam and impart the intensity modulation of the electron beam at radio frequency and an electron beam dump. The rotator then imparts the radio frequency modulated x-rays 206 toward the target 203.

The radio-frequency modulated tube is a high voltage, high energy tube. The radio-frequency modulated tube may be, for example, a Klystron, such as is known in the art. Suitable implementations for the X-ray source 209 are commercially available off the shelf. For example, the NIR MCP-PMT and X-Ray Scintillator line of products offered by Hamamatsu Corp. offer several suitable alternatives. Hamamatsu Corp. can be reached in the United States at: 360 Foothill Rd. Bridgewater, N.J. 08807, ph. 908-231-0960; fax: 908-231-1218. Additional information can be obtained through those contacts or at www.hamamatsu.com over the World Wide Web of the Internet.

Figure 3A:
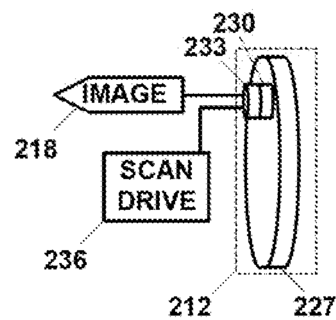
FIG. 3A-FIG. 3B illustrate the scanning of the detector array across the back of the microchannel plate in the sensor of the embodiment in FIG. 1.

The sensor 212 of the illustrated embodiment comprises three parts as shown in FIG. 3A. It includes a layer of a scintillating material 227 capable of intercepting the X-rays 215 emanating from the target volume 203 and fluorescing light (not shown) correlated thereto. A radio-frequency modulated microchannel plate 230 is located behind the scintillating material 227 to detect and amplify the fluoresced light. The microchannel plate 230 may also be referred to as a "phase plate". The amplification of the fluoresced light may also be described as "intensifying" the image, and so the microchannel plate 230 may be considered an "image intensifier". A detector array 233 is placed to detect the amplified fluorescent light output by the radio-frequency modulated microchannel plate 230. Again, suitable implementations are commercially available off the shelf, including the X-Ray Scintillator line of products offered by Hamamatsu Corp. mentioned above. Furthermore, information regarding imaging with such sensors and their fabrication is available from U.S. Pat. Nos. 6,531,225 and 6,762,420.

Figure 3B:
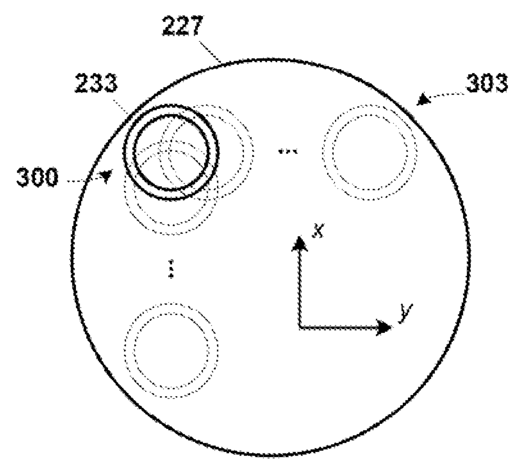

In the particular embodiment illustrated in FIG. 3B, the detector array 233 is not large enough to cover the entire back of the microchannel plate 230 simultaneously. The illustrated embodiment therefore includes a scan drive 236 that scans the detector array 233 from one position 300, shown in FIG. 3B in solid lines, to other positions 303 (only one indicated), shown in broken lines, across the back 231 of the microchannel plate 236. Such scan drives are known to the art and the scan drive 236 can be implemented using any suitable scan drive known to the art.

The X-ray source 209 receives a modulation signal 239 from a radio-frequency ("RF") modulator 242. The sensor 212 receives a modulation signal 238 from the RF modulator 244. The signals 238, 239 are "synced" by the sync 245 in that they are harmonically related to one another. Such a harmonic relationship can be achieved many ways and so the sync 245 may be implemented in many ways. Some embodiments may use a direct digital synthesizer ("DDS") for this function, but those skilled in the art having the benefit of this disclosure will appreciate that any suitable technique known to the art may be employed.

The radio frequency modulation can include modulation of amplitude, phase and/or frequency from a few kilohertz (e.g., 3 KHz) through 300 GHz and is applied across the two faces of the microchannel plate 230. Those in the art will recognize that, practically, the state of art in x-ray fluorescent imaging materials is at ~10 GHz, but "direct detection" of x-ray energy by new solid state detectors may very well have growth to 300 GHz. Typically, modulation will hold on one center frequency and amplitude/phase modulate, although some embodiments may modulate all three at once. This creates a biasing of the microchannel plate 230 that changes the recorded intensity of the image 218 as a function of the transmitted radio frequency modulated X-ray energy.

In operation, the source 209 generates the X-rays 206. The radio frequency amplitude modulated X-rays 206 have a preferred conical angle α of radiation from the tube volume toward the desired target volume 203 to be examined. The expanding cone α of X-rays 206 from the virtual point source of the source 209 provides a means for casting a magnified shadow of an object placed in the path between the X-ray source 209 and a scintillator material 227. The reflected X-rays 215 through the target volume 203 will also contain this radio frequency modulation, containing energy modified by the materials in the object to be X-ray imaged.

The microwave modulation of the X-Rays 215 allows detection of second and third harmonics and their products. The X-Rays 215 induce photocurrents/fields generated by the nonlinear material of the sample 203. The photocurrents induce stress/strain on material lattice at frequency and the strained lattice induces x-ray diffraction pattern changes at frequency. The X-ray detected ratio of harmonics to carrier power can then be used to identify diffraction pattern elements originating from the nonlinear thin film. The mechanics of these phenomena are further discussed in Y. H. Yu, et al., "Measurement of Thin Film Piezoelectric Constants Using X-ray Diffraction Technique", Phys. Scr. T129 (2007) 353-357 (2007); and A. B. Kozyrev, et al., "Nonlinear Behavior of Thin Film SrTiO3 Capacitors at Microwave Frequencies", 84 J. App. Phys. 3326-3332 (1998). Both of these papers are incorporated by reference below.

The reflected X-rays 215 intercept the scintillation material 227 in front of the radio frequency modulated microchannel plate 230. The scintillation material 227 fluoresces across an optical frequency range that the microchannel plate 230 is designed to amplify. The scintillation material 227 has a time constant small enough that the amplitude of the fluorescence follows the radio frequency modulation rate. The resulting modulated microchannel plate light (not shown) is detected by the detector array 233 and recorded as the digital image 218. More particularly, scintillator materials have 100 ps (10 GHz) fluorescence response. The fluorescence typically peaks in the near IR to visible and IR to Visible wavelength detector diodes with bandwidths >10 GHz are commercially available off the shelf.

Some embodiments may use "soft" x-ray detectors rather than scintillator materials. Soft x-ray detectors ~10 keV have 100 ps (10 GHz) direct detection response. This approach trades higher frequency x-ray resolution for smaller detection receiver (no fluorescence layer, no high voltage micro channel plate) and easier to produce x-ray sources. Direct detection X-ray detectors with 10 μm×10 μm pixel resolution arrays are commercially available off the shelf.

Returning to FIG. 2, the resulting amplitude image 218 is a set of ordered data. As those in the art having the benefit of this disclosure will appreciate, the image 218 may be rendered for human perception by means of printed hardcopy or electronic display. However, such rendering can be omitted in some embodiments. The processing and analysis can therefore be performed directly on the image 218 regardless of whether it is rendered. In practice, a series of images 218 are captured over time, each representing a sampling of the reflected X-rays 215. The image 218 may be stored, rendered for human perception, processed for some further use, or any combination thereof depending upon the particular embodiment.

Figure 4:
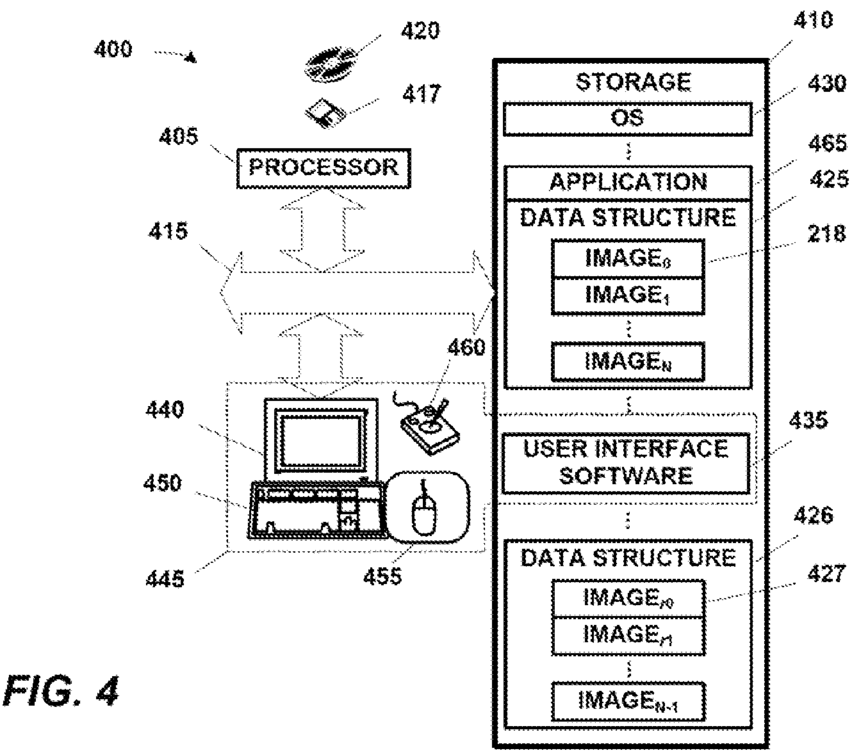
FIG. 4 shows selected portions of the hardware and software architecture of a computing apparatus such as may be employed in some aspects of the embodiments disclosed herein.

The X-ray microscopy imaging system 200 shown in FIG. 2 will typically be deployed in association with a computing apparatus 400, shown in FIG. 4. The computing apparatus 400 in the illustrated embodiment is a stand-alone work station. In alternative embodiments, the computing apparatus may be embedded in the apparatus 200 or may be part of a larger computing system. Instead of a workstation, the computing apparatus could be implemented in a desktop, laptop, notebook, etc., in other embodiments. The present invention admits wide variation in the implementation of the computing apparatus 400.

In one aspect, the present invention is a software implemented method for generating and analyzing an X-ray image. FIG. 4 shows selected portions of the hardware and software architecture of the computing apparatus 400 such as may be employed in some aspects of the present invention. The computing apparatus 400 includes a processor 405 communicating with storage 410 over a bus system 415.

The present invention admits wide variation in the implementation of the processor 405. Certain types of processors may be more desirable than others for some embodiments. For instance a digital signal processor ("DSP") or graphics processor may be more desirable for the illustrated embodiment than will be a general purpose microprocessor. Other video handling capabilities might also be desirable. For instance, a Joint Photographic Experts Group ("JPEG") or other video compression capability and/or multi-media extension may be desirable. In some embodiments, the processor 405 may be implemented as a processor set, such as a microprocessor with a graphics co-processor particularly for server architectures.

The storage 410 may be implemented in conventional fashion and may include a variety of types of storage, such as a hard disk and/or random access memory ("RAM") and/or removable storage such as a magnetic disk (not shown) or an optical disk (also not shown). The storage 410 will typically involve both read-only and writable memory. The storage 410 will typically be implemented in magnetic media (e.g., magnetic tape or magnetic disk), although other types of media may be employed in some embodiments (e.g., optical disk). The storage 410 may also employ various virtual memory and other memory management techniques. The present invention admits wide latitude in implementation of the storage 410 in various embodiments. In the illustrated embodiment, the storage 410 is internal memory implemented in a hard disk main memory, RAM, and in cache.

The bus system 415 will also vary widely by implementation. Depending upon the implementation, the bus system 415 may comprise an internal bus, a network backbone, or some combination thereof. For example, if the computing apparatus 400 is instead embedded with the X-ray microscopy imaging system 200, the bus system 415 may be implemented as an internal bus. On the other hand, if the computing apparatus 400 is but a part of a larger computing system across which the computing functionalities are distributed, then some type of external bus—i.e., a network backbone—will be employed. Either way, the bus system 415 may be implemented using conventional technologies.

The storage 410 is also encoded with an operating system ("OS") 430, user interface software 435, and an application 465. The user interface software 435, in conjunction with a display 440, implements a user interface 445. The user interface 445 may include peripheral input/output devices such as a keypad or keyboard 450, a mouse 455, or a joystick 460. The processor 405 runs under the control of the operating system 430, which may be practically any operating system known to the art. The application 465 may be invoked by the operating system 430 upon power up, reset, or both, depending on the implementation of the operating system 430. The application 465, when invoked, performs the method of the present invention. The user may also invoke the application 465 in conventional fashion through the user interface 445.

The storage 410 is also encoded with two data structures 425, 426. The data structure 425 contains the images 218 (only one indicated) that are acquired as described above. The data structure 426 contains the resultant images 427 (only one indicated) generated by the application 465 through the process generally described above. The resulting images 427 are "angle only" radiograph images with intensity proportional to signal strength of the difference between the transmitted and received modulation frequencies and their harmonics. The images now give a standard radiograph with the benefit of referencing the detected harmonic signals to the appropriate angle/pixel location in the image. The data structures 425, 426 may be implemented in any suitable type of data structure known to the art, such as a database, a list, or a queue. The data structures 425, 426 may be designed for long term storage of the images 218, 427 or to temporarily buffer them, depending on the implementation.

As mentioned above, the hardware and software architecture shown in FIG. 4 is exemplary only, and may find wide variation across numerous alternative embodiments. A good example of such variation is the implementation of the data structures 425, 426 described immediately above. Another good example is in the application 465. In other embodiments, the functionality residing in the application 465 may instead repose in some other kind of software component, such as a script, a daemon, etc.

There similarly may be variation in the suns of the various elements of the software aspects of the architecture. For example, there is no need for the images 218, 427 to reside on the same computing apparatus 400 or to reside on the same computing apparatus 400 as the application 465 by which they are processed and created. Some embodiments of the present invention may be implemented on a computing system comprising more than one computing apparatus. Such computing system may employ a network client/server architecture. In a networked client/server architecture the images 218, 427 (only one of each indicated) may, for example, reside on a data structure (not shown) residing on a server while the application by which they are processed resides on a workstation. Furthermore, there is no requirement that the images all reside together. The images 218 might reside on the server while the resultant images 427 might reside on a workstation. The invention admits wide variation in this respect.

Note that there is no requirement such a computing system be networked. Alternative embodiments may employ, for instance, a peer-to-peer architecture or some hybrid of a peer-to-peer and client/server architecture. The size and geographic scope of the computing system 500 is not material to the practice of the invention. The size and scope may range anywhere from just a few machines of a Local Area Network ("LAN") located in the same room to many hundreds or thousands of machines globally distributed in an enterprise computing system.

As is apparent from the discussion above, some portions of the detailed descriptions herein are consequently presented in terms of a software implemented process involving symbolic representations of operations on data bits within a memory in a computing system or a computing device. These descriptions and representations are the means used by those in the art to most effectively convey the substance of their work to others skilled in the art. The process and operation require physical manipulations of physical quantities. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated or otherwise as may be apparent, throughout the present disclosure, these descriptions refer to the action and processes of an electronic device, that manipulates and transforms data represented as physical (electronic, magnetic, or optical) quantities within some electronic device's storage into other data similarly represented as physical quantities within the storage, or in transmission or display devices. Exemplary of the terms denoting such a description are, without limitation, the terms "processing," "computing," "calculating," "determining," "displaying," and the like.

Note also that the software implemented aspects of the invention are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The invention is not limited, by these aspects of any given implementation.

Furthermore, portions of this disclosure include discussion of "images". These images are shown in a human-perceptible form, i.e., in a hard copy. Note that this presentation is for the sake of illustration. The images are actually collections or sets of ordered data. In the illustrated embodiments, the data is three-dimensional. The images may be rendered to make them perceptible by image analysts in some embodiments. For example, the images may be rendered for output in hard copy, or they may be rendered and displayed electronically. However, some embodiments of the invention may be practiced automatically, that is, without human interaction. Thus, some embodiments may be practiced without the images being so rendered.

Figure 5:
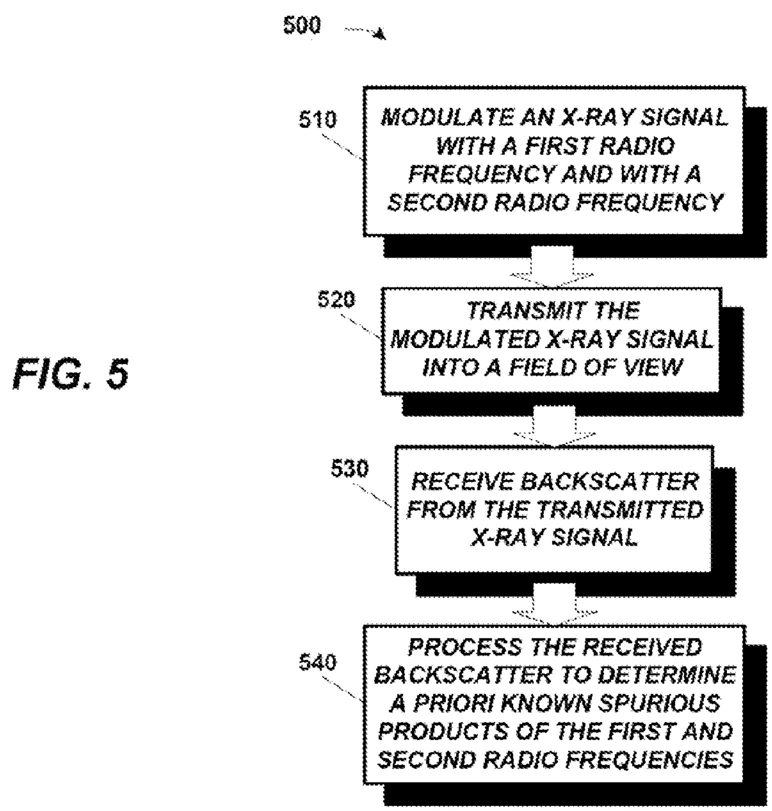
FIG. 5 illustrates a method in a different aspect of the present invention.

In operation, the application 465 of the illustrated embodiment executes the process 500 shown in FIG. 5. The process 500 may be performed in two parts—image acquisition and image processing in some embodiments. In this particular embodiment, all acquisition occurs prior to processing. Alternative embodiments may "process on the fly", or process the images 218, shown in FIG. 2, as they are acquired. The difference will create some differences in handling having both advantages and disadvantages relative to the illustrated embodiment. Those in the art having the benefit of this disclosure will appreciate not only these relative advantages and disadvantages, but also the differences in handling and will be able to implement such alternatives should they wish to do so.

As mentioned, in one aspect, the present invention provides a method, such as the method 500 illustrated in FIG. 5. The method 500 comprises modulating (at 510) an X-ray signal with a first radio frequency and with a second radio frequency. The modulated X-ray signal is then transmitted (at 520) into a field of view. Backscatter from the transmitted X-ray signal is received (at 530) and processed (at 540) to determine a prior known or expected spurious products—e.g., sum and/or difference products for the first and second frequencies with which the X-ray signals 206 are modulated. This is done by performing a time series analysis to detect image change across the time series of images that represent pixels changing at the rate of the difference frequency of the RF frequency and the a priori signature harmonic patterns.

More particularly, because the first and second frequencies are known, it is known what harmonic patterns of spurious products might be expected. Examples of spurious products include $2f_1+3f_2$ and/or $3f_2-2f_1$, as well as other permutations in sums and differences. The spurious products that are detectable and detected will form a pattern characteristic of the material of the sample under inspection. Such patterns can be determined for materials of interest and, for example, stored electronically for later matching with images acquired from the sample as described above. The material can thus be identified.

The invention admits some latitude in the implementation of both the apparatus and method of the invention. For example, a suitable handled X-ray device suitable for modification to implement the presently disclosed technique is the LEXID™ X-ray Imaging Device available from Physical Optics Corporation, at 0600 Gramercy Place, Torrance, Calif. 90501-1821 Phone: 310-320-3088, Fax: 310-320-5961. In particular, the device would be modified to implement the modulation technique disclosed herein. Additional information is available over the World Wide Web of the Internet at their website <http://www.poc.com/default.asp>, Principles of operation, construction, and design are also disclosed in U.S. Pat. No. 7,231,017.

Using such a handheld device, however, the computing apparatus 400 of FIG. 4 will more typically be embodied in a laptop. The laptop will receive the received backscatter from a sensor through a peripheral connection from a handheld sensor. The processing may even be performed in the handheld sensor itself in some embodiments. Such an acquisition is shown in U.S. application Ser. No. 12/541,539, entitled "X-Ray Explosive Imager", in the name of the inventor J. Richard Wood, and filed Aug. 14, 2009, commonly assigned herewith, and incorporated by reference below.

The technique can be used to identify electronics under examination. Some materials may have a unique harmonic response, that given some it priori knowledge about the target sample being x-ray interrogated, may give a unique identifying signal. While the technique disclosed herein will produce a very low rate of false alarms, it also will generally suffer form a low signal to noise ratio. However, under even very good condition, the signal to noise ratio will be ~0.5 with conventional RF detection. Accordingly, this is not a strong negative relative to conventional techniques.

The following applications, patents, and papers are hereby incorporated by reference in their entirety and for all purposes as if set forth herein verbatim:

U.S. Provisional Application Ser. No. 61/566,584, entitled "Modulated X-Ray Harmonic Detection", in the name of the inventor J. Richard Wood, and filed Dec. 2, 2011, and commonly assigned herewith; and U.S. Provisional Application Ser. No. 61/089,140, entitled "X-Ray Explosive Imager", in the name of the inventor J. Richard Wood, and filed Aug. 15, 2008, and commonly assigned herewith; and U.S. Provisional Application Ser. No. 61/107,924, entitled "X-Ray RADAR", in the name of the inventor J. Richard Wood, and filed Oct. 23, 2008, and commonly assigned herewith; and U.S. application Ser. No. 12/604,548, entitled "X-Ray RADAR", in the name of the inventor J. Richard Wood, and filed Oct. 23, 2009, and commonly assumed herewith.

U.S. application Ser. No. 12/541,539, entitled "X-Ray Explosive Imager", in the name of the inventor J. Richard Wood, and filed Aug. 14, 2009, and commonly assigned herewith.

Y. H. Yu, et al., "Measurement of Thin Film Piezoelectric Constants Using X-ray Diffraction Technique", Phys. Scr. T129 (2007) 353-357 (2007).

A. B. Kozyrev, et al., "Nonlinear Behavior of Thin Film SrTiO3 Capacitors at Microwave Frequencies", 84 J. App. Phys. 3326-3332 (1998).

In the event of conflict between the present disclosure and any incorporated reference, the present disclosure controls.

The phrase "capable of" as used herein is a recognition of the fact that some functions described for the various parts of the disclosed apparatus are performed only when the apparatus is powered and/or in operation. Those in the art having the benefit of this disclosure will appreciate that the embodiments illustrated herein include a number of electronic or electro-mechanical parts that, to operate, require electrical power. Even when provided with power, some functions described herein only occur when in operation. Thus, at times, some embodiments of the apparatus of the invention are "capable of" performing the recited functions even when they are not actually performing them—i.e., when there is no power or when they are powered but not in operation.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:

concurrently modulating an X-ray signal with a first radio frequency signal and with a second radio frequency signal to generate a modulated X-ray signal;

transmitting the modulated X-ray signal into a field of view containing a sample;

receiving backscatter of the modulated X-ray signal reflected from the sample; and processing the backscatter to identify the sample from a pattern of detected harmonics of the first radio frequency signal and the second radio frequency signal.

2. The method of claim 1, wherein the backscatter is generated by diffraction of the modulated X-ray signal by the sample.

3. The method of claim 1, wherein the detected harmonics include spurious harmonic products of the first radio frequency signal and the second radio frequency signal.

4. The method of claim 1, wherein processing the backscatter to identify the sample includes comparing a detected harmonic pattern against a plurality of a priori known harmonic pattern signatures.

5. An X-ray RADAR apparatus, comprising:

means for concurrently modulating an X-ray signal with a first radio frequency signal and with a second radio frequency signal to generate a modulated X-ray signal;

means for transmitting the modulated X-ray signal into a field of view containing a sample;

means for receiving backscatter of the modulated X-ray signal reflected from the sample; and means for processing the backscatter to identify the sample from a pattern of detected harmonics of the first radio frequency signal and the second radio frequency signal.

6. The X-ray RADAR apparatus of claim 5, wherein the detected harmonics include spurious harmonic products of the first radio frequency signal and the second radio frequency signal.

7. The X-ray RADAR apparatus of claim 5, wherein processing the backscatter to identify the sample includes comparing a detected harmonic pattern against a plurality of a priori known harmonic pattern signatures.

8. The X-ray RADAR apparatus of claim 5, further comprising means for collimating the modulated X-ray signal before the transmitting.

9. A computer-implemented method, comprising:

receiving data representative of backscatter of a radio frequency modulated X-ray signal reflected from a sample, the radio frequency modulated X-ray signal being concurrently radio frequency modulated with a first radio frequency signal and with a second radio frequency signal; and processing the data to identify the sample from a pattern of detected harmonics of the first radio frequency signal and the second radio frequency signal.

10. The computer-implemented method of claim 9, wherein the data is generated by diffraction of the radio frequency modulated X-ray signal by the sample.

11. The computer-implemented method of claim 9, wherein the detected harmonics include spurious harmonic products of the first radio frequency signal and the second radio frequency signal.

12. The computer-implemented method of claim 9, wherein processing the data to identify the sample includes comparing a detected harmonic pattern against a plurality of a priori known harmonic pattern signatures.

13. A program storage medium encoded with instructions that, when executed by a processor, perform a software implemented method, the software implemented method comprising:

receiving data representative of backscatter of a radio frequency modulated X-ray signal reflected from a sample, the radio frequency modulated X-ray signal being radio frequency modulated concurrently with a first radio frequency signal and with a second radio frequency signal; and processing the data to identity the sample from a pattern of detected harmonics of the first radio frequency signal and the second radio frequency signal.

14. The program storage medium of claim 13, wherein the data is generated by diffraction of the radio frequency modulated X-ray signal by the sample.

15. The program storage medium of claim 13, wherein the detected harmonics include spurious harmonic products of the first radio frequency signal and the second radio frequency signal.

16. The program storage medium of claim 13, wherein processing the data to identify the sample includes comparing a detected harmonic pattern against a plurality of a priori known harmonic pattern signatures.

17. A computing apparatus, comprising:

a processor;

a bus system;

a storage communicating with the processor over the bus system; and an application residing on the storage that, when invoked by the processor, performs a software implemented method, comprising:

receiving data representative of backscatter of a radio frequency modulated X-ray signal reflected from a sample, the radio frequency modulated X-ray signal being radio frequency modulated concurrently with a first radio frequency signal and with a second radio frequency signal; and processing the data to identify the sample from a pattern of detected harmonics of the first radio frequency signal and the second radio frequency signal.

18. The computing apparatus of claim 17, wherein processing the data to identify a sample includes comparing the detected harmonic pattern against a plurality of a priori known harmonic pattern signatures.

19. An X-ray RADAR apparatus, comprising:

a transmitter capable of:

concurrently modulating an X-ray signal with a first radio frequency signal and with a second radio frequency signal to generate a modulated X-ray signal; and transmitting the modulated X-ray signal into a field of view;

a receiver capable of receiving backscatter of the modulated X-ray signal reflected from a sample within the field of view; and a processing unit capable of processing the backscatter to identify the sample from a pattern of detected harmonics of the first radio frequency signal and the second radio frequency signal.

20. The X-ray RADAR apparatus of claim 19, wherein the processing unit comprises:

a processor;

a bus system;

a storage communicating with the processor over the bus system; and an application residing on the storage that, when invoked by the processor, performs a software implemented method, comprising:

processing the backscatter to identify the sample from the pattern of the detected harmonics of the first radio frequency signal and the second radio frequency signal.

* * * * *